(12) United States Patent
Nagel et al.

(10) Patent No.: US 9,956,338 B2
(45) Date of Patent: May 1, 2018

(54) DRUG DELIVERY DEVICE

(71) Applicant: SANOFI-AVENTIS DEUTSCHLAND GMBH, Frankfurt am Main (DE)

(72) Inventors: Thomas Nagel, Tharandt (DE); Rene Richter, Tharandt (DE); Robert Witt, Dresden (DE); Richard Guenther, Dresden (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 94 days.

(21) Appl. No.: 14/405,992

(22) PCT Filed: Jul. 5, 2013

(86) PCT No.: PCT/EP2013/064293
§ 371 (c)(1),
(2) Date: Dec. 5, 2014

(87) PCT Pub. No.: WO2014/006197
PCT Pub. Date: Jan. 9, 2014

(65) Prior Publication Data
US 2015/0126928 A1    May 7, 2015

(30) Foreign Application Priority Data
Jul. 6, 2012  (EP) .................................... 12175388

(51) Int. Cl.
*A61M 5/00*    (2006.01)
*A61M 5/142*   (2006.01)
(Continued)

(52) U.S. Cl.
CPC ....... *A61M 5/14212* (2013.01); *A61K 9/0004* (2013.01); *A61M 5/14593* (2013.01);
(Continued)

(58) Field of Classification Search
CPC ..... A61M 2005/14513; A61M 5/14593; F04B 43/06; B01L 2400/0418; B01L 2400/0415; B01L 2400/0421
See application file for complete search history.

(56) References Cited

U.S. PATENT DOCUMENTS 3,923,426 A * 12/1975 Theeuwes ............. F04B 17/003
                                                    204/630
4,525,164 A *  6/1985 Loeb ................. A61M 5/14244
                                                    128/DIG. 12
(Continued)

FOREIGN PATENT DOCUMENTS

CN      101432032 A    5/2009
JP      2005-503242 A  2/2005
(Continued)

OTHER PUBLICATIONS

Chinese Search Report for Chinese Patent Application No. 201380034991.9, dated Sep. 25, 2016.
(Continued)

*Primary Examiner* — Emily Schmidt
*Assistant Examiner* — William Carpenter
(74) *Attorney, Agent, or Firm* — McDonnell Boehnen Hulbert & Berghoff LLP

(57) ABSTRACT

The invention relates to a drug delivery device, comprising a control unit, a drive unit, a pressurizing medium container arranged to contain a pressurizing liquid, a drug container arranged to contain a drug and a discharge nozzle, wherein the drive unit when controlled and energized by the control unit is arranged to generate a pressure gradient in the pressurizing liquid thereby propagating the pressure to the drug container and at least partially displacing the drug from the drug container through the discharge nozzle, wherein the drive unit is arranged as an electro-osmotic actor.

8 Claims, 2 Drawing Sheets

(51) Int. Cl.
*A61K 9/00* (2006.01)
*A61M 5/145* (2006.01)

(52) U.S. Cl.
CPC ............ *A61M 2005/14268* (2013.01); *A61M 2005/14513* (2013.01); *A61M 2205/502* (2013.01)

(56) References Cited

U.S. PATENT DOCUMENTS

| | | | |
|---|---|---|---|
| 6,283,853 | B1 | 9/2001 | Pellenc et al. |
| 6,283,953 | B1* | 9/2001 | Ayer .................... A61K 9/0004 424/423 |
| 6,406,605 | B1* | 6/2002 | Moles ...................... F15C 5/00 137/833 |
| 6,485,626 | B1* | 11/2002 | Bottani ............ G01N 27/44704 204/451 |
| 6,770,183 | B1* | 8/2004 | Hencken ............... F04B 19/006 204/600 |
| 2002/0070116 | A1* | 6/2002 | Ohkawa .............. B01L 3/50273 204/603 |
| 2003/0013186 | A1* | 1/2003 | Martin .................. B01D 57/02 604/891.1 |
| 2003/0088238 | A1* | 5/2003 | Poulsen .............. A61M 5/1413 604/890.1 |
| 2004/0144646 | A1 | 7/2004 | Theeuwes et al. |
| 2005/0247558 | A1* | 11/2005 | Anex ................. A61M 5/14248 204/275.1 |
| 2006/0052768 | A1* | 3/2006 | Joshi .................... A61K 9/0004 604/892.1 |
| 2006/0122577 | A1 | 6/2006 | Poulsen et al. |
| 2007/0062250 | A1 | 3/2007 | Krulevitch et al. |
| 2008/0033338 | A1* | 2/2008 | Smith .................. A61M 31/002 604/20 |
| 2008/0102119 | A1 | 5/2008 | Grovender et al. |
| 2009/0129945 | A1* | 5/2009 | Adleff ................... A61M 5/145 417/53 |

FOREIGN PATENT DOCUMENTS

| | | |
|---|---|---|
| JP | 2006-513031 A | 4/2006 |
| JP | 2007-521887 A | 8/2007 |
| JP | 2008-504794 A | 2/2008 |
| JP | 2013-521885 A | 6/2013 |
| WO | 2004/069390 A1 | 8/2004 |
| WO | 2005/113419 | 12/2005 |
| WO | 2009/048144 A1 | 4/2009 |
| WO | 2009/119519 A1 | 10/2009 |
| WO | 2011/112723 | 9/2011 |
| WO | WO 2011112723 A2 * | 9/2011 ........ A61M 5/14248 |

OTHER PUBLICATIONS

Chinese Office Action for Chinese Patent Application No. 201380034991.9 dated Oct. 9, 2016.
International Search Report for Int. App. No. PCT/EP2013/064293, completed Sep. 20, 2013.
Japanese Office Action for JP Application No. 2015-519236, dated Apr. 18, 2017.

* cited by examiner

DRUG DELIVERY DEVICE

CROSS REFERENCE TO RELATED APPLICATIONS

The present application is a U.S. National Phase Application pursuant to 35 U.S.C. § 371 of International Application No. PCT/EP2013/064293 filed Jul. 5, 2013, which claims priority to European Patent Application No. 12175388.3 filed Jul. 6, 2012. The entire disclosure contents of these applications are herewith incorporated by reference into the present application.

TECHNICAL FIELD

The invention relates to a drug delivery device.

BACKGROUND

Many medicaments have to be injected into the body. This applies in particular to medicaments, which are deactivated or have their efficiency remarkably decreased by oral administration, e.g. proteines (such as Insulin, growth hormones, interferons), carbohydrates (e.g. Heparin), antibodies and the majority of vaccines. Such medicaments are predominantly injected by means of syringes, medicament pens or medicament pumps.

SUMMARY

It is an object of the present invention to provide an improved drug delivery device.

The object is achieved by a drug delivery device according to claim 1.

Preferred embodiments of the invention are given in the dependent claims.

According to the invention a drug delivery device comprises a control unit, a drive unit, a pressurizing medium container arranged to contain a pressurizing liquid, a drug container arranged to contain a drug and a discharge nozzle, wherein the drive unit when controlled and energized by the control unit is arranged to generate a pressure gradient in the pressurizing liquid thereby propagating the pressure to the drug container and at least partially displacing the drug from the drug container through the discharge nozzle, wherein the drive unit is arranged as an electro-osmotic actor.

Electro-osmosis is the movement of a liquid in parallel to a surface due to an electrical field. The cause of this effect is that a liquid is internally electrically neutral while developing an electrochemical double layer on its surface. The thickness of the double layer depends on the ions dissolved in the liquid. Thus, the surface of the liquid is not electrically neutral. If an electrical field is applied in parallel to the surface the liquid is subjected to a force so that a current forms. This effect does only work for electrically insulating surfaces of the electro-osmotic actor as electrical conductors would short-circuit a field in parallel to the surface.

The drug delivery device according to the invention allows for reducing the space requirements as opposed to drug delivery devices driven by conventional mechanical pumps. Furthermore, the drug delivery device according to the invention has a particularly low part count and provides improved handling.

In an exemplary embodiment the electro-osmotic actor may comprise a solid state body with at least one capillary and is arranged to apply an electrical field essentially in parallel to a surface of the pressurizing liquid within the capillary.

In another exemplary embodiment the electro-osmotic actor may comprise a membrane with traversing pores and is arranged to apply an electrical field essentially in parallel to a surface of the pressurizing liquid within the pores. The membrane may be flexible.

The membrane may be a fabric with conducting means shaped as a membrane with varying pore size along its thickness, so that the pore walls are smooth and inclined with respect to an electric field applied normally to said fabric. The fabric may comprise electrodes and porous conducting layers, to which an electric signal can be applied, and non-conducting porous layers between the membrane and the electrodes, preventing direct contact between the electrode and membranes. An absorbing layer may be placed onto the electrode on the side of drying. Alternatively, the absorbing layer could be omitted, or other layers could be added outside the electrodes.

The membrane may also be a fabric with a conducting means shaped as a membrane with cylindrical straight pores. The non-conducting layers may constitute part of the same physical membrane.

In an exemplary embodiment the pressurizing liquid is water, particularly distilled water.

In another exemplary embodiment the pressurizing liquid is a liquid carbon hydride, such as an alcohol.

The drug delivery device may comprise a reusable and a disposable unit. The reusable part comprises at least a control unit.

In an exemplary embodiment, a disposable unit for a drug delivery device comprises a drug container, a pressurizing medium container and an electro-osmotic actor, wherein the drug container is configured to be attached to a discharge nozzle, and wherein the electro osmotic actor is configured to displace a pressurizing liquid from the pressurizing medium container so as to expel a drug from the drug container through the discharge nozzle.

In an exemplary embodiment a flexible membrane may be arranged within the drug container for separating the drug from the pressurizing liquid.

In another exemplary embodiment the control unit, the electro-osmotic actor and the pressurizing medium container are arranged within a reusable module such that only the drug container and the discharge nozzle are disposable. Thus the amount of waste and the ecological footprint are reduced.

In yet another exemplary embodiment the control unit and the electro-osmotic actor are arranged within a reusable module such that only the drug container, the discharge nozzle and the pressurizing medium container are disposable. Thus the amount of waste and the ecological footprint are reduced.

In yet another exemplary embodiment the control unit is arranged within a reusable module, wherein the electro-osmotic actor is arranged as an electro-osmotic membrane within the pressurizing medium container, wherein the pressurizing medium container and the drug container are arranged as compartments separated by the flexible membrane within a shared container.

In yet another exemplary embodiment the control unit, the electro-osmotic actor and the pressurizing medium container are arranged within a reusable module, wherein the electro-osmotic actor is arranged as an electro-osmotic membrane within the pressurizing medium container such that only the drug container and the discharge nozzle are disposable. Thus the amount of waste and the ecological footprint are reduced.

In an exemplary embodiment the control unit comprises a user interface so as to allow for controlling doses, flow rates etc. and/or monitor user compliance.

In an exemplary embodiment the discharge nozzle is arranged as an injection needle.

In another exemplary embodiment the discharge nozzle is arranged as a jet nozzle.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
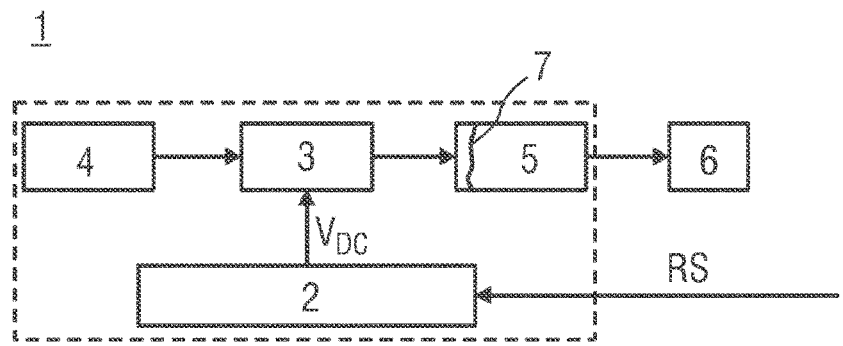
FIG. 1 is a schematic view of a drug delivery device.

FIG. 1 is a schematic view of a drug delivery device 1 comprising a control unit 2 with a user interface, an electro-osmotic actor 3, a pressurizing medium container 4 containing a pressurizing liquid, a drug container 5 containing a drug and a discharge nozzle 6 arranged as an injection needle or jet nozzle. The pressurizing medium container 4 is in fluid communication with the drug container 5 via the electro-osmotic actor 3. The discharge nozzle 6 is in fluid communication with the drug in the drug container 5.

Upon receiving a request signal RS, e.g. caused by a user operation, the control unit 2 applies a DC voltage $V_{DC}$ to the electro-osmotic actor 3 for generating a pressure gradient in the pressurizing liquid such that the pressurizing liquid is pumped from the pressurizing medium container 4 into the drug container 5. In an alternative embodiment of the electro-osmotic actor 3, an AC voltage or a mixture of an AC and DC voltage is applied by the control unit 2. Thus, electrolysis of the pressurizing liquid may be prevented, especially when water is used as pressurizing liquid. The drug container 5 comprises a flexible membrane 7 separating the drug from the pressurizing liquid but allowing propagation of the pressure from the pressurizing liquid to the drug. Hence, the liquid drug is delivered through the discharge nozzle 6 to the patient. The control unit 2 serves for controlling and energizing the electro-osmotic actor 3. The pressurizing liquid may be an aqueous solution, e.g. water, particularly distilled water or at least one liquid carbohydrate, such as an alcohol.

An electrical connection between the control unit 2 and the electro-osmotic actor 3 may also be configured to allow for a feedback to the control unit 2, e.g. for processing data of sensors which may be arranged with the electro-osmotic actor 3 so that a dose and/or flow rate may be close-loop controlled.

The electro-osmotic actor 3 comprises a solid state body with at least one capillary and is arranged to apply an electrical field essentially in parallel to a surface of the pressurizing liquid within the capillary.

Figure 2:
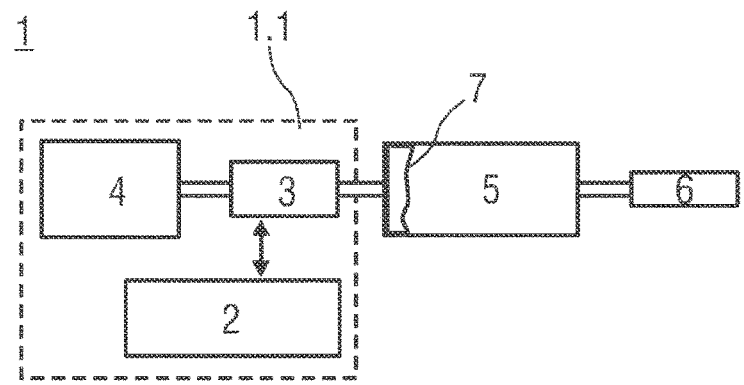
FIG. 2 is a schematic view of an embodiment of the drug delivery device.

FIG. 2 is a schematic view of an embodiment of the drug delivery device 1 with a reusable module 1.1 comprising the control unit 2, the electro-osmotic actor 3 and the pressurizing medium container 4, while the drug container 5 and the discharge nozzle 6 are disposable.

Figure 3:
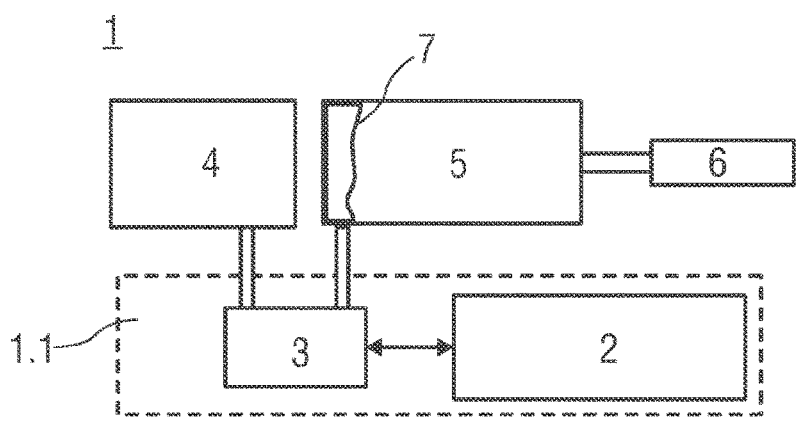
FIG. 3 is a schematic view of another embodiment of the drug delivery device.

FIG. 3 is a schematic view of an embodiment of the drug delivery device 1 with a reusable module 1.1 comprising the control unit 2 and the electro-osmotic actor 3 while the pressurizing medium container 4, the drug container 5 and the discharge nozzle 6 are disposable.

Figure 4:
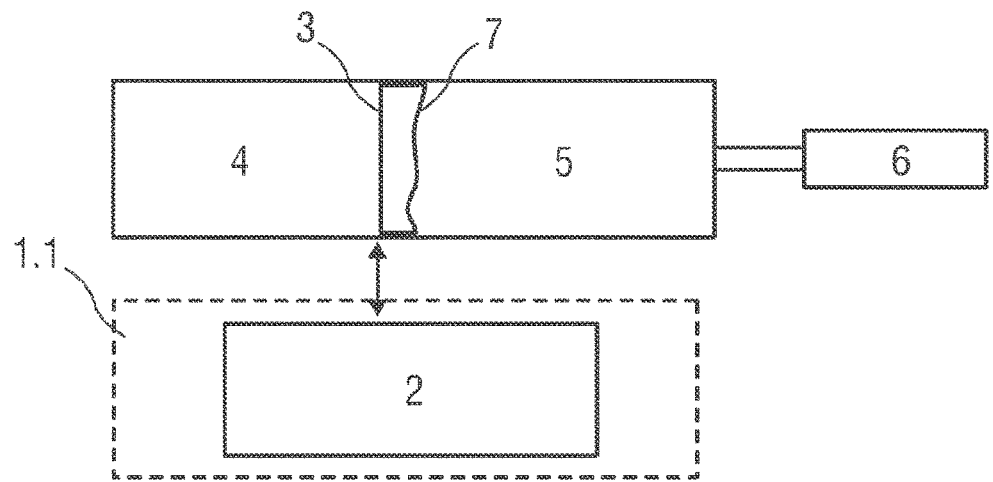
FIG. 4 is a schematic view of yet another embodiment of the drug delivery device.

FIG. 4 is a schematic view of an embodiment of the drug delivery device 1 with a reusable module 1.1 comprising the control unit 2 while the electro-osmotic actor 3, the pressurizing medium container 4, the drug container 5 and the discharge nozzle 6 are disposable. The electro-osmotic actor 3 is arranged as an electro-osmotic pump membrane within the pressurizing medium container 4. The pressurizing medium container 4 and the drug container 5 are arranged as compartments separated by the flexible membrane 7 within a shared container 4, 5.

The electro-osmotic actor 3 comprises a membrane with traversing pores and is arranged to apply an electrical field essentially in parallel to a surface of the pressurizing liquid within the pores.

Figure 5:
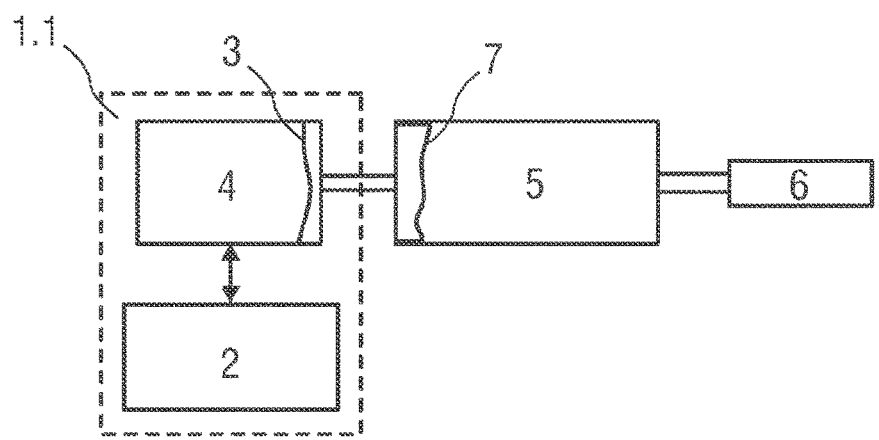
FIG. 5 is a schematic view of yet another embodiment of the drug delivery device.

FIG. 5 is a schematic view of an embodiment of the drug delivery device 1 with a reusable module 1.1 comprising the control unit 2, the electro-osmotic actor 3 and the pressurizing medium container 4, while the drug container 5 and the discharge nozzle 6 are disposable, wherein the electro-osmotic actor 3 is arranged as an electro-osmotic pump membrane within the pressurizing medium container 4.

The invention claimed is:

1. A drug delivery device, comprising a control unit, a drive unit, a pressurizing medium container arranged to contain a pressurizing liquid, a disposable drug container arranged to contain a drug and connected to a disposable discharge nozzle, wherein the drive unit when controlled and energized by the control unit is arranged to generate a pressure gradient in the pressurizing liquid thereby propagating the pressure to the drug container and at least partially displacing the drug from the drug container through the discharge nozzle, wherein the drive unit is arranged as an electro-osmotic actor, wherein the electro-osmotic actor comprises a first flexible membrane with traversing pores and is arranged to apply an electrical field essentially in parallel to a surface of the pressurizing liquid within the pores, wherein the electro-osmotic actor is arranged as an electro-osmotic membrane within the pressurizing medium container, wherein a second flexible membrane is arranged within the drug container for separating the drug from the pressurizing liquid, wherein the control unit, the electro-osmotic actor and the pressurizing medium container are physically contained together and arranged in connection to each other within a single reusable unit, where the reusable unit is designed to removably connect to the drug container such that the drug container is retained outside of the reusable unit and the drug container and the connected discharge nozzle can be disconnected from the reusable unit for disposable and a second disposable drug container can then be connected to the reusable unit.

2. Drug delivery device according to claim 1, wherein the pressurizing liquid is water.

3. Drug delivery device according to claim 2, wherein the pressurizing liquid is distilled water.

4. Drug delivery device according to claim 1, wherein the pressurizing liquid is a liquid carbon hydride.

5. Drug delivery device according to claim 4, wherein the liquid carbon hydride is an alcohol.

6. Drug delivery device according to claim 1, wherein the control unit comprises a user interface.

7. Drug delivery device according to claim 1, wherein the discharge nozzle is arranged as an injection needle or as a jet nozzle.

8. The drug delivery device of claim 1 where the first flexible comprises a conducting fabric having electrodes and porous conducting layers.

* * * * *